`US008372123B2`

(12) United States Patent
Smisson, III et al.

(10) Patent No.: US 8,372,123 B2
(45) Date of Patent: Feb. 12, 2013

(54) STERNAL CLOSURE DEVICE AND METHOD OF USING SAME

(75) Inventors: Hugh F. Smisson, III, Macon, GA (US); David C. Field, Snellville, GA (US); Paul Gombar, Sr., Powder Springs, GA (US); Paul Gombar, Jr., Winder, GA (US); Richard Griffith, Covington, GA (US); Joseph Suarez, Atlanta, GA (US); Brandi Bohleber, Macon, GA (US)

(73) Assignee: Trimax Medical Management, Inc., Macon, GA (US)

( * ) Notice: Subject to any disclaimer, the term of this patent is extended or adjusted under 35 U.S.C. 154(b) by 761 days.

(21) Appl. No.: 11/953,557

(22) Filed: Dec. 10, 2007

(65) Prior Publication Data

US 2008/0140128 A1 Jun. 12, 2008

Related U.S. Application Data (60) Provisional application No. 60/869,148, filed on Dec. 8, 2006.

(51) Int. Cl.
*A61B 17/58* (2006.01)
(52) U.S. Cl. ......................................... 606/280; 606/246
(58) Field of Classification Search .................... 606/69, 606/70, 71, 72, 73, 246–279, 280–299, 60
See application file for complete search history.

(56) References Cited

U.S. PATENT DOCUMENTS

| | | | |
|---|---|---|---|
| 4,279,248 A | 7/1981 | Gabbay | |
| 4,957,496 A | 9/1990 | Schmidt | |
| 5,108,395 A | 4/1992 | Laurain | |
| 6,007,538 A | 12/1999 | Levin | |
| 6,051,007 A | 4/2000 | Hogendijk et al. | |
| 6,302,883 B1 * | 10/2001 | Bono | 606/291 |
| 6,306,136 B1 * | 10/2001 | Baccelli | 606/279 |
| 6,402,756 B1 * | 6/2002 | Ralph et al. | 606/71 |
| 6,540,769 B1 * | 4/2003 | Miller, III | 606/216 |
| 6,699,249 B2 * | 3/2004 | Schlapfer et al. | 606/71 |
| 6,712,821 B2 * | 3/2004 | Gabbay | 606/71 |
| 6,872,210 B2 | 3/2005 | Hearn | |
| 6,969,398 B2 * | 11/2005 | Stevens et al. | 606/216 |
| 7,033,377 B2 * | 4/2006 | Miller, III | 606/213 |
| 7,052,499 B2 | 5/2006 | Steger et al. | |
| 7,090,676 B2 | 8/2006 | Huebner et al. | |
| 7,186,256 B2 * | 3/2007 | Michelson | 606/71 |
| 7,189,237 B2 | 3/2007 | Huebner | |
| 7,214,226 B2 * | 5/2007 | Alleyne | 606/86 A |
| 7,288,095 B2 | 10/2007 | Baynham et al. | |

(Continued)

OTHER PUBLICATIONS

International Search Report dated Jun. 26, 2008 for PCT/US07/86993.

*Primary Examiner* — Kevin T Truong
*Assistant Examiner* — Christopher Beccia
(74) *Attorney, Agent, or Firm* — Sutherland Asbill & Brennan LLP (57) ABSTRACT

A sternal closure device is provided, comprising a first plate having a bone fixation region with at least one countersunk aperture for receiving a fastening means for affixing the first plate to one side of the sternum, and a locking region with at least one protruding aligning member; a second plate having a bone fixation region with at least one countersunk aperture for receiving a fastening means for affixing the second plate to the opposite side of the sternum, and a locking region dimensioned to contact at least a portion of the locking region of the first plate; and a rotating member that engages with the aligning member(s) on the first plate for holding the first and second plates together to secure the opposite sides of the sternum. The first and second plates can be separated by reversibly disengaging the rotating member from the aligning member(s).

24 Claims, 4 Drawing Sheets

U.S. PATENT DOCUMENTS

| | | | |
|---|---|---|---|
| 7,303,564 B2 * | 12/2007 | Freid et al. | 606/86 B |
| 7,635,364 B2 * | 12/2009 | Barrall et al. | 606/70 |
| 7,635,366 B2 * | 12/2009 | Abdou | 606/71 |
| 2004/0030342 A1 * | 2/2004 | Trieu et al. | 606/72 |
| 2004/0204712 A1 * | 10/2004 | Kolb et al. | 606/69 |
| 2005/0124996 A1 * | 6/2005 | Hearn | 606/71 |
| 2006/0058798 A1 * | 3/2006 | Roman et al. | 606/71 |
| 2007/0043371 A1 * | 2/2007 | Teague et al. | 606/71 |

* cited by examiner

STERNAL CLOSURE DEVICE AND METHOD OF USING SAME

CROSS REFERENCE TO RELATED APPLICATIONS

This application claims priority pursuant to 35 U.S.C. §119 based upon Provisional Application Ser. No. 60/869,148 filed Dec. 8, 2006, the entire disclosure of which is hereby incorporated by reference.

FIELD OF THE INVENTION

The present invention relates generally to the repair of bone fractures, and more particularly to a method and device for closing opposite sides of a patient's sternum across a fracture.

BACKGROUND OF THE INVENTION

Many surgical procedures require a median sternotomy, a procedure in which an incision is made along the sternum such that it can be separated laterally into two sides. This allows access to the tissues and organs located in a patient's thoracic cavity. Following the surgical procedure, the two sides of the sternum must be closed. When a medical emergency occurs after the sternum has been closed, physicians need to be able to immediately reopen the sternum to access the patient's thoracic cavity.

Closure of the sternum was traditionally performed using wire based closure systems. Stainless steel wires were wrapped around or through the sides of the sternum to secure the sides together. Wire based closure systems have several recognized deficiencies. Their attachment is time consuming, averaging 15-20 minutes, and they do not allow for quick access to the thoracic cavity in cases where emergency re-entry is necessary. Wire based closure systems also promote post-surgery complications including patient pain, infection, and problems with healing caused by the wire loosening and allowing the sides of the sternum to slide with respect to each other. Such complications often require the patient to undergo a follow-up surgical procedure.

Other types of closure systems have been developed as alternatives to wire based closure systems. For example, clamp closure devices and plate closure devices are newer sternal closure technologies.

U.S. Pat. No. 6,007,538 discloses a pair of slidably associated J-shaped clamp members. The curved end of each clamp member wraps around one of the patient's ribs, and the straight ends extend across the fracture and overlap one another. The straight ends have threaded holes, and the holes of the two straight ends are aligned to receive screws. The sternum may be reopened by removing the screws from the clamp members on each side of the sternum and sliding the clamp members away from each other.

U.S. Pat. No. 7,033,377 discloses a clamp closure device wherein the clamp members are held together by a rotary lock member. The sternum may be reopened by using a plier-like tool to open the rotary lock and then a prying tool to force the clamp members apart.

U.S. Pat. No. 7,052,499 discloses an elongated plate with two regions suited to receive fastening devices for fixation to the sternum, and a bridge region therebetween. The sternum can be reopened by cutting the bridge region, which is designed for such cutting.

U.S. Pat. No. 6,872,210 discloses a sternum closure device with two overlapping plates or clamps that are held together by a release member. Movement or removal of the release member allows for separation of the two sides of the sternum.

These examples and other sternum closure devices have numerous deficiencies. For example, due to cumbersome release mechanisms, the prior art devices may not have smooth edges or a low profile for minimizing patient discomfort; the release member may not be flush with the top and/or side surfaces of the device, thereby leaving a protruding object in the patient's chest; and opening the device may be too time consuming to allow the physician immediate access to the thoracic cavity in case of medical emergency. Opening the device may involve ruining the device itself requiring a new device to re-close the sternum, which is costly and time consuming. Opening or removing the device may involve multiple tiny pieces, such as screws, that are hard to manipulate and can get lost in the patient's body. Further, when screws have to be removed to open the device and then re-inserted into the bone to re-close the sternum, it results in weaker fastening of the device to the sternum. Alternatively, the device may have a design that allows for quick reopening, but compromises stabilization of the opposing sides of the sternum, which is important during healing. It would, therefore, be desirable to provide a new and improved sternum closure device that overcomes these drawbacks and limitations.

SUMMARY OF THE INVENTION

A sternal closure device and methods of use are provided to repair a sternum across a fracture.

In one aspect, the sternal closure device includes a first plate, which has a bone fixation region with at least one countersunk aperture for receiving a fastening means for affixing the first plate to one side of the sternum and a locking region with at least one protruding aligning member. The device also includes a second plate, which has a bone fixation region with at least one countersunk aperture for receiving a fastening means for affixing the second plate to the opposite side of the sternum and a locking region dimensioned to contact at least a portion of the locking region of the first plate. The device further includes a rotating member that engages with the aligning member(s) on the first plate for holding the first and second plates together to secure the opposite sides of the sternum. The first and second plates can be separated by reversibly disengaging the rotating member from the aligning member(s).

In a preferred embodiment, the locking region of the second plate overlaps with at least a portion of the locking region of the first plate. In a further embodiment, the locking region of the second plate comprises an aperture that extends over a portion of the locking region of the first plate when the locking regions are overlapped. In one embodiment, the first plate comprises at least two aligning members. In another embodiment, the second plate comprises at least one aligning member. In a preferred embodiment, the aligning members are pegs. The rotating member engages the aligning member(s) to hold the first and second plates together. It will be appreciated by the skilled artisan that many various alternative locking mechanisms can be adapted which still achieve the objectives of minimizing the profile (thickness or height), protrusions and separate components of the present sternal closure device.

In a preferred embodiment, the sternal closure device includes a lower plate, which has a bone fixation region with at least one countersunk aperture for receiving a fastening means for affixing the lower plate to one side of the sternum and a locking region with at least one protruding aligning member. The device also includes an upper plate, which has a bone fixation region with at least one countersunk aperture for receiving a fastening means for affixing the upper plate to the opposite side of the sternum and an attached aperture dimensioned to overlap with at least a portion of said locking region of said lower plate. The device further includes a rotating member dimensioned to engage with said at least one protruding aligning member when rotated in a first direction, for holding the lower and upper plates together to secure the opposite sides of the sternum. The rotating member can be removed and the lower and upper plates separated by reversely rotating the rotating member to disengage it from the aligning member(s).

In another aspect, a method is provided for repair of a sternal fracture using a sternal closure device. The method can comprise affixing a first plate to one side of the sternum using fastening means through at least one countersunk aperture in the first plate, affixing a second plate to the opposite side of the sternum using fastening means through at least one countersunk aperture in the second plate, and holding the first and second plates together by engaging a rotating member with at least one aligning member on the first plate.

BRIEF DESCRIPTION OF THE DRAWINGS

The objects and advantages of the present invention will be better understood and more readily apparent when considered in conjunction with the following detailed description and accompanying drawings which illustrate, by way of example, a preferred embodiment and in which.

DETAILED DESCRIPTION OF THE PREFERRED EMBODIMENTS

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

An improved sternal closure device has been developed for use in closing the sternum following a median sternotomy. The sternal closure device provides a means of quickly separating the plates to gain access to the patient's thoracic cavity in case of medical emergency. The sternal closure device also provides maximum stabilization of the sides of the sternum together. Preferably, the sternal closure device has a smooth, low-profile design.

Advantageously, the sternal closure device herein can help reduce the time required to close the sternum following a surgical procedure, as well as the time required to reopen the sternum in case of a medical emergency. The device is also beneficial post-operation, as it can help reduce patient pain and has a low risk of the sides of the sternum sliding with respect to each other.

In one aspect, the sternal closure device includes a first plate, which has a bone fixation region with at least one countersunk aperture for receiving a fastening means for affixing the first plate to one side of the sternum and a locking region with at least one protruding aligning member. The device also includes a second plate, which has a bone fixation region with at least one countersunk aperture for receiving a fastening means for affixing the second plate to the opposite side of the sternum and a locking region dimensioned to contact at least a portion of the locking region of the first plate. The device further includes a rotating member that engages with the aligning member(s) on the first plate for holding the first and second plates together to secure the opposite sides of the sternum. The first and second plates can be separated by reversibly disengaging the rotating member from the aligning member(s).

In a preferred embodiment, the sternal closure device includes a lower plate, which has a bone fixation region with at least one countersunk aperture for receiving a fastening means for affixing the lower plate to one side of the sternum and a locking region with at least one protruding aligning member. The device also includes an upper plate, which has a bone fixation region with at least one countersunk aperture for receiving a fastening means for affixing the upper plate to the opposite side of the sternum and an attached aperture dimensioned to overlap with at least a portion of said locking region of said lower plate. The device further includes a rotating member dimensioned to engage with said at least one protruding aligning member when rotated in a first direction, for holding the lower and upper plates together to secure the opposite sides of the sternum. The rotating member can be removed and the lower and upper plates separated by reversely rotating the rotating member to disengage it from the aligning member(s).

In another aspect, a method is provided for repair of a sternal fracture using a sternal closure device. The method can comprise affixing a first plate to one side of the sternum using fastening means through at least one countersunk aperture in the first plate, affixing a second plate to the opposite side of the sternum using fastening means through at least one countersunk aperture in the second plate, and holding the first and second plates together by engaging a rotating member with at least one aligning member on the first plate.

The sternal closure device can be further understood with reference to the exemplary, non-limiting embodiment illustrated in FIGS. 1-7.

Figure 1:
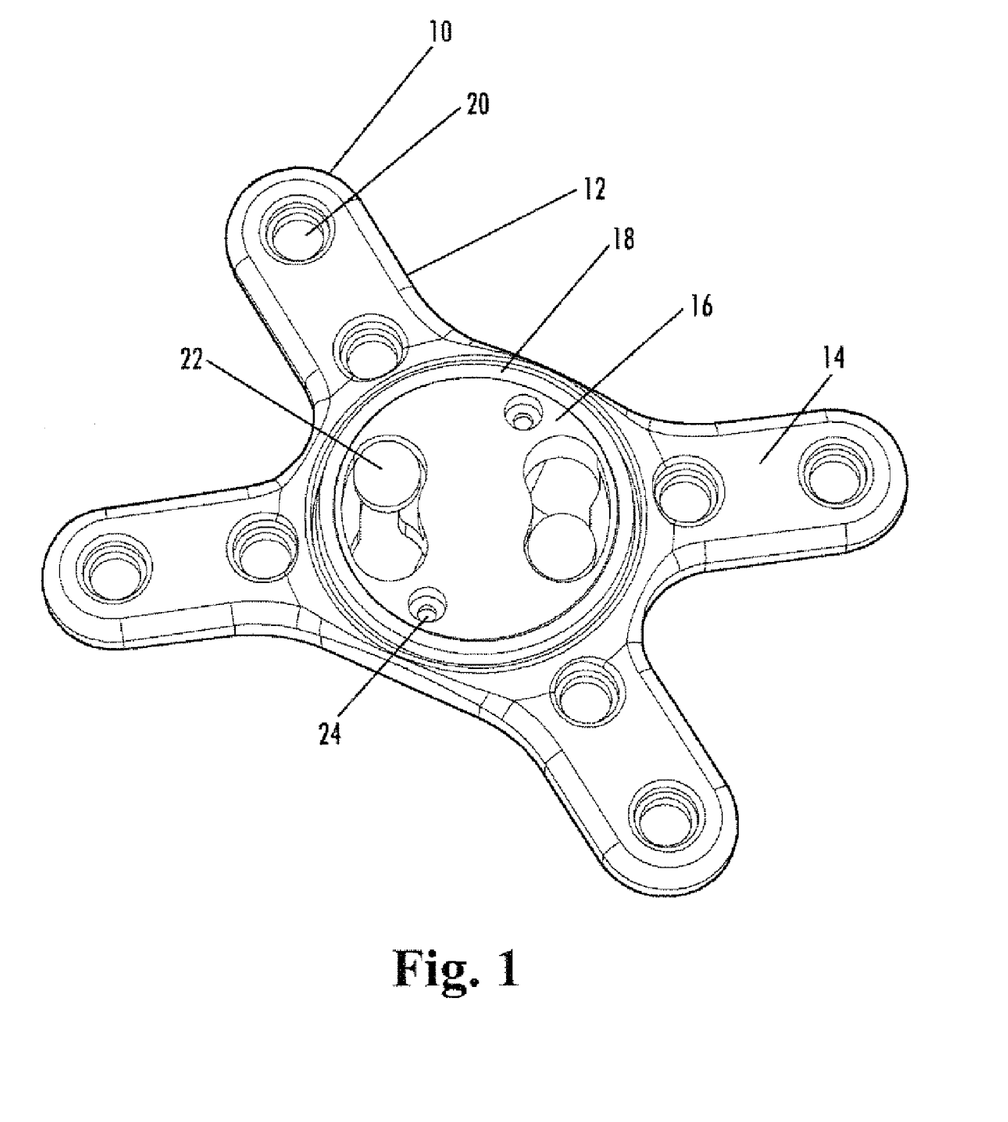
FIG. 1 is a perspective view of one embodiment of the sternal closure device, shown in the assembled state.

One embodiment of the sternal closure device is shown in FIG. 1. The sternal closure device 10 includes a first plate 12, a second plate 14, a rotating member 16, and a retaining ring 18. The first and second plates 12, 14 can be used to hold together the severed sides of the sternum by affixing each plate to one side of the sternum and securing the plates 12, 14 together with the rotating member 16. The sternal closure device 10 can be made from any biocompatible material, including, but not limited to, stainless steel and titanium. The device 10 can also be constructed with a variety of therapeutic coatings, such as antibiotic, antiviral or congealing compositions.

The shape of the first and second plates 12, 14 can vary widely. The first and second plates 12, 14 should be shaped and sized to extend to or across the sternal fracture but not beyond the outer edge of each side of the sternum. Additionally, the first and second plates 12, 14 can be shaped and sized such that the length (the direction extending along the medial sternal fracture) of the locking region 26 of the first plate 12 is at least about 50%, 60%, 70%, or more of the length of the device 10. The shape and size can be adjusted to accommodate a range of sternum sizes. In exemplary embodiments, the length of the device 10 is about 15 mm to 40 mm or about 20 mm, and the width (the direction extending across the sternum) of the device 10 is about 20 mm to 50 mm or about 35 mm. In preferred embodiments, the diameter of the rotating member 16 is about 10 mm to 30 mm or about 11 mm. In preferred embodiments, the height of the device 10 is about 1 mm to 2 mm or about 1.5 mm.

The first and second plates 12, 14 are each shown to include four countersunk apertures 20. The number of countersunk apertures 20 can range from one to several per plate. The number and placement of countersunk apertures 20 is selected to keep each plate tightly secured to the sternum. The countersunk apertures 20 should be sized to conform with the fastening means used, both the width of the aperture and the depth of the countersunk portion. Preferably, the top surface of each fastening means is approximately flush with the top surface 40 of the rotating member 16. A variety of fastening means can be used, including those known in the art, such as screws. The fastening means may be threaded. The countersunk apertures 20 may be threaded to receive the threaded portion of a fastening means. Alternatively, the countersunk apertures 20 may be non-threaded.

Various embodiments of the sternal closure device 10 may incorporate shielding devices or locking screws to prevent post-operative extrusion of the fastening means, which has long been a matter of clinical concern. Depending on the condition of the patient, the type of surgery, or the surgeon's healing strategy, it may be desirable to maintain complete fixation of the fastening means or to allow a certain amount of post-operative extrusion. When no extrusion is desired, locking screws can be used as the fastening means. Locking screws are locked in place at their fully threaded position, thereby preventing extrusion.

Alternatively, in some cases post-operative motion by fastening means, such as screws, may be desired to allow the formation of stronger new bone and lessen the stress on the first and second plates 12, 14. Even when some extrusion is beneficial, extrusion beyond a certain point can be dangerous. A shielding device may be incorporated that will allow fastening means to extrude at least partially following their placement, will protect surrounding tissue from contact with the fastening means, and will prevent further egress and even encourage ingress once the fastening means have passed the beneficial point of extrusion. In various embodiments, shielding frames may be completely detachable from or movably attached to the first and second plates 12, 14 adjacent the countersunk apertures 20. In a first position, the shielding frames allow access to the countersunk apertures 20 for operative placement of the fastening means. Following such placement, the shielding frames may be secured in a second position above the fastening means. The shielding frames are preferably not in direct contact with the fastening means initially, to allow some amount of extrusion. The shielding frames may be constructed of a flexible material that provides increasing resistance to extrusion of a fastening means once a fastening means has come into direct contact with a shielding frame.

Figure 2:
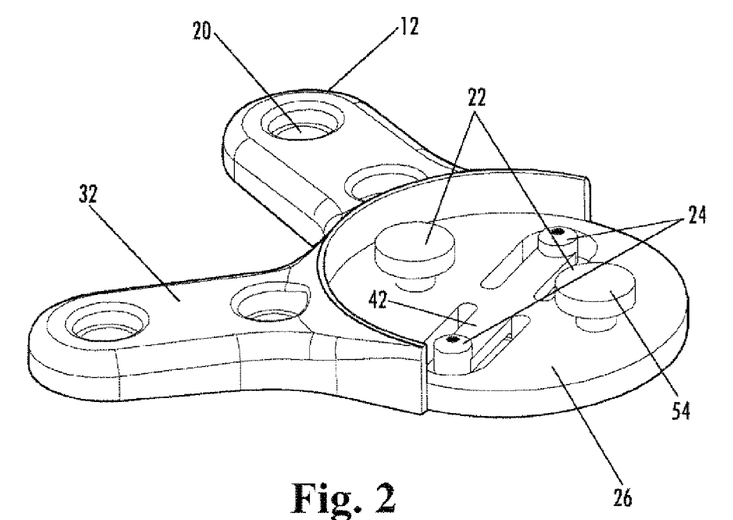
FIG. 2 is a perspective view of the first plate element of the embodiment shown in FIG. 1.
Figure 3:
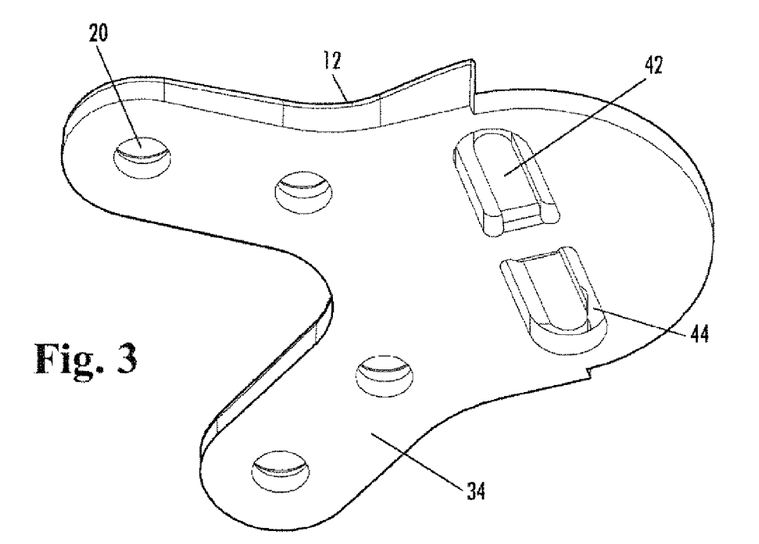
FIG. 3 is a perspective posterior view of the first plate element of the embodiment shown in FIG. 1.

As shown in FIGS. 2 and 3, the first plate 12 has a top surface 32 and a sternum-contacting surface 34. The locking region 26 is shown to be depressed from the top surface 32 of the first plate 12. The locking region 26 comprises two protruding aligning members 22, which are shown as pegs. The locking mechanism can differ in various embodiments to include a different number of protruding pegs or to include protruding aligning members 22 of a different shape, size, or design. The aligning members 22 are designed to engage with the rotating member 16, such that the rotating member 16 is held in place when rotated to a first position and is released when reversely rotated to a second position.

Figure 4:
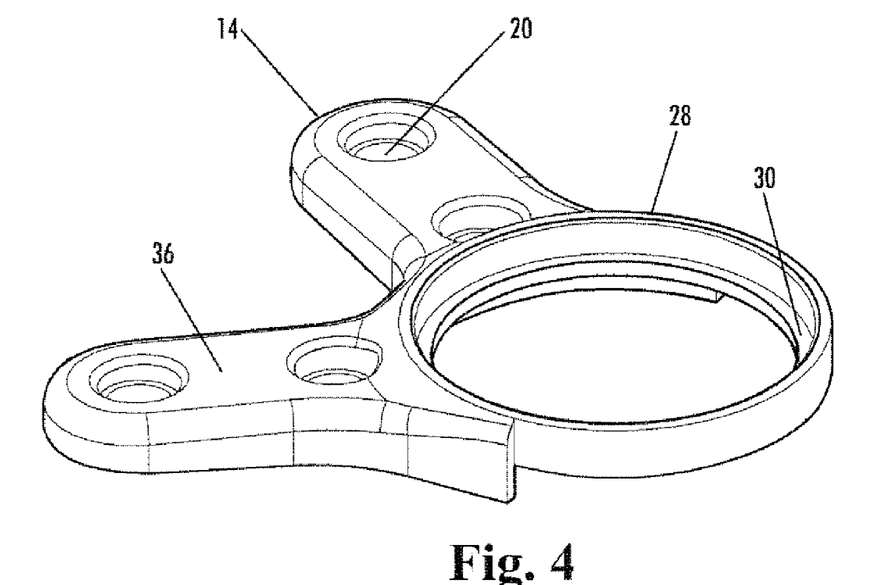
FIG. 4 is a perspective view of the second plate element of the embodiment shown in FIG. 1.
Figure 5:
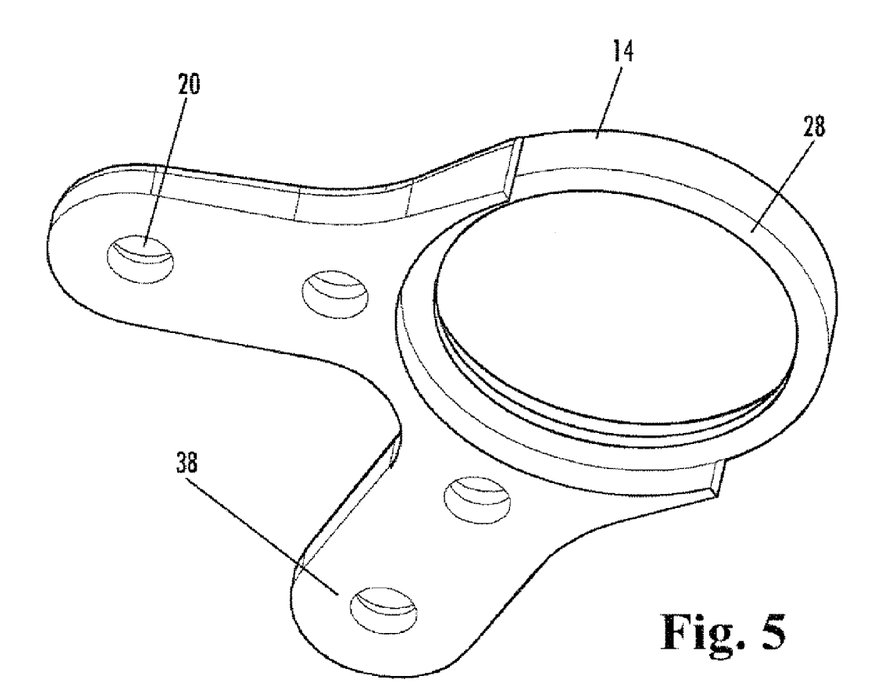
FIG. 5 is a perspective posterior view of the second plate element of the embodiment shown in FIG. 1.

As shown in FIGS. 4 and 5, the second plate 14 has a top surface 36 and a sternum-contacting surface 38. The second plate 14 is shown to have an interior shelf 30. In one embodiment, the rotating member 16 sits atop the interior shelf 30. The locking region 28 of the second plate 14 contacts at least a portion of the locking region 26 of the first plate 12. The locking regions 26, 28 may sit adjacent to each other, without any overlap. The locking region 26 of the first plate 12 may extend across the sternal fracture. The locking region 28 of the second plate 14 may overlap the locking region 26 of the first plate 12 and also extend across the sternal fracture, as in the embodiment shown in the figures. In such an embodiment, the first plate 12 is the lower plate, and the second plate 14 is the upper plate. The locking region 28 of the second plate 14 may comprise an aperture that extends over a portion of the locking region 26 of the first plate 12 when the locking regions 26, 28 of the first plate 12 and second plate 14 are overlapped, as in the embodiment shown in the figures.

In various embodiments, the locking region 28 of the second plate 14 may have at least one protruding aligning member. In such embodiments, the rotating member 16 engages with the aligning members on both the first and second plates 12, 14 at the same time, and the rotating member 16 is held in place with respect to the plates 12, 14 when rotated to a first position and is released when reversely rotated to a second position.

The rotating member 16 secures the first and second plates 12, 14 together and prevents them from moving with respect to each other. Accordingly, the sides of the sternum are secured in a way that prevents them from moving with respect to each other. The rotating member 16 may be any shape, including an oval, a square, or a rounded square. In a preferred embodiment, it is round. The rotating member 16 may be only partially rotatable. In various embodiments, the rotating member can engage and disengage with the aligning member(s) by rotating a quarter turn or less in a forward and reverse direction, respectively.

Figure 6:
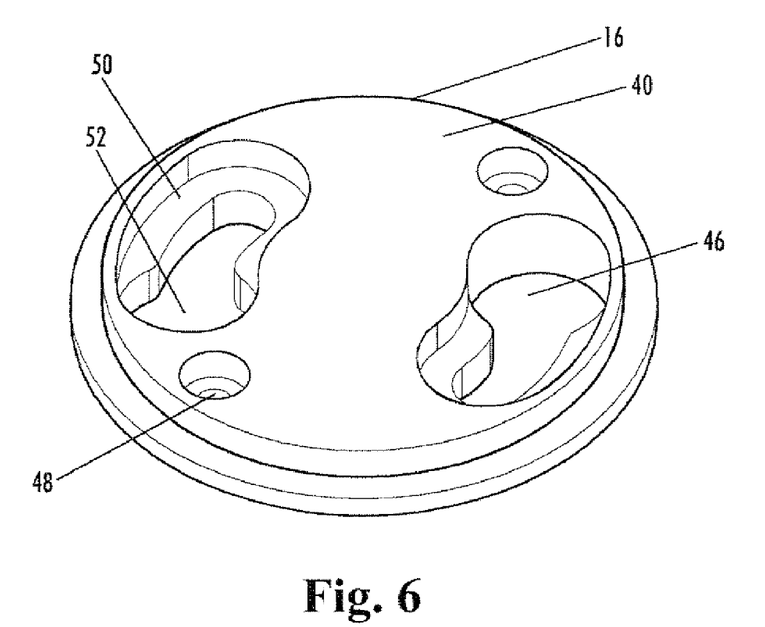
FIG. 6 is a perspective view of the rotating member element of the embodiment shown in FIG. 1.

Referring to FIGS. 2 and 6, the rotating member 16 is shown to be round and to include two types of apertures—peg holes 46 dimensioned to engage with the protruding peg aligning members 22, and pin holes 48 dimensioned to engage with the depressible pins 24. The peg holes 46 have a countersunk portion 50 and a wide portion 52 that fits around the head 54 of the peg aligning member 22. The locking mechanism is engaged by aligning the rotating member 16 such that the wide portion 52 of the peg holes 46 are over the pegs 22 and sliding the peg holes 46 down over the pegs 22, such that the rotating member 16 sits atop the mated first and second plates 12, 14. The rotating member 16 is then rotated in one direction until the head 54 of each peg 22 is above the countersunk portion 50 of the respective peg hole 26 and each pin 24 comes through the respective pin hole 48. Given the engagement of the pegs 22 and the pins 24 with the rotating member 16, the locking mechanism is secure and cannot be loosened or disengaged by the stresses of implantation in the chest. Further, in its locked position, the device 10 provides a strong, rigid system across the sternal fracture to maximally stabilize the sides of the sternum.

When the rotating member 16 is deliberately disengaged from the locking mechanism and removed, the first and second plates 12, 14 are able to separate. In various embodiments the locking regions 26, 28 of the first plate 12 or second plate 14 may include a release mechanism. The embodiment of the first plate 12 shown in FIG. 1 includes a release mechanism comprising two pins 24. The pins 24 of FIG. 1 are located at the ends of lever-like structures 42, as shown in FIG. 2. The levers 42 are each surrounded by a thin cut-out 44, allowing depression of the pins 24. The pins 24 may be depressed simultaneously for release using a two-ended tool, for example. The rotating member 16 can be disengaged from the locking mechanism by simultaneously depressing the optional depressible pins 24, rotating the rotating member 16 in a reverse direction until the wide portion 52 of the peg holes 46 are aligned with the head 54 of each peg 22, and lifting the rotating member 16 to remove it. The invention provides that one or more of such locking pegs or depressible pins can be used to facilitate locking and release. This allows the plates to be separated quickly in case of a medical emergency.

The release mechanism could take a variety of configurations known to one of skill in the art, for example pins or spring-loaded detents. The release mechanism may enable one-handed release, meaning the release mechanism could be engaged and the rotating member rotated and removed with a single hand. Alternatively, the release mechanism could be engaged with one hand while a second hand is used to rotate and remove the rotating member. The release mechanism can be structurally separate from the aligning members, as in the embodiment shown, or it can be incorporated into the aligning members. In one embodiment, the aligning members are spring-loaded, and squeezing the aligning members from their locked position to a second position enables release of the rotating member.

Figure 7:
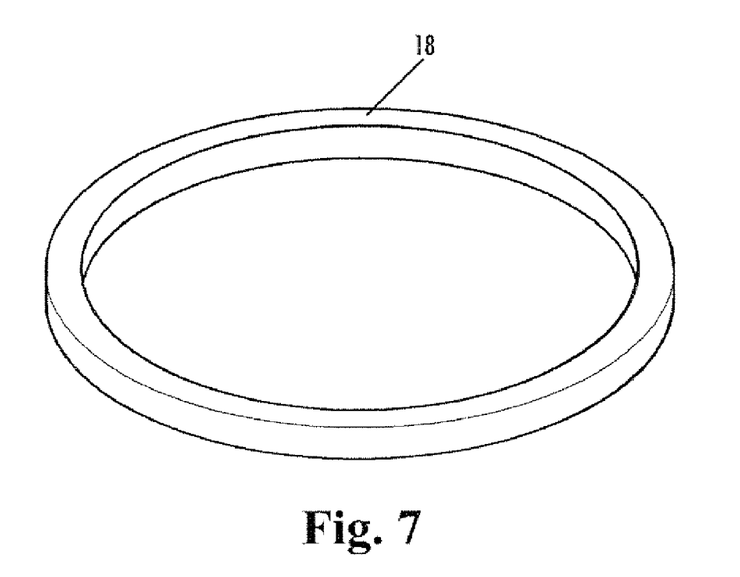
FIG. 7 is a perspective view of the retaining ring element of the embodiment shown in FIG. 1.

FIG. 7 shows an optional retaining ring 18, which fits around the rotating member 16 when seated on the mated first and second plates 12, 14. The retaining ring 18 can be used to facilitate retention of the rotating member prior to locking and smooth rotation thereof.

These and other features and embodiments of the present invention will be apparent to those in the art in view of the present disclosure.

What is claimed is:

1. A sternal closure device comprising:
   a) a first plate forming a top surface and an opposite sternum-facing surface, and having a bone fixation region with at least one countersunk aperture for receiving a fastening means for affixing said sternum-facing surface of said first plate to one side of the sternum, and a locking region with at least one aligning member protruding approximately perpendicular to the top surface of said plate;
   b) a second plate forming a top surface and an opposite sternum-facing surface, and having a bone fixation region with at least one countersunk aperture for receiving a fastening means for affixing sternum-facing surface of said second said plate to an opposite side of the sternum, and a locking region dimensioned to contact at least a portion of said locking region of said first plate; and
   c) a rotating member having at least one aperture that engages with said at least one aligning member on said first plate for holding said first and second plates together to secure opposite sides of the sternum, wherein said first and second plates can be separated by disengaging said rotating member from said at least one aligning member.

2. The device of claim 1, wherein said locking region of said second plate overlaps with at least a portion of said locking region of said first plate.

3. The device of claim 2, wherein said locking region of said second plate comprises an aperture that extends over a portion of said locking region of said first plate when said locking regions are overlapped.

4. The device of claim 1, wherein said at least one aligning member comprises at least one protruding peg.

5. The device of claim 1, wherein said locking region of said second plate comprises at least one aligning member.

6. The device of claim 5, wherein said rotating member engages said at least one aligning member on said first plate and said at least one aligning member on said second plate.

7. The device of claim 1, wherein said first plate and said second plate each have at least two countersunk apertures.

8. The device of claim 1, wherein said first plate, said second plate, and said rotating member are made of titanium.

9. A method of treating a sternal fracture comprising affixing to a patient the sternal closure device of claim 1.

10. A method of treating a sternal fracture using the sternal closure device of claim 1, the method comprising:
    a) affixing said first plate to one side of the sternum using said fastening means through said at least one countersunk aperture;
    b) affixing said second plate to opposite side of the sternum using said fastening means through said at least one countersunk aperture; and
    c) holding said first and second plates together by engaging said rotating member with said at least one aligning member on said first plate.

11. A sternal closure device for securing sides of a sternum across a fracture comprising:
    a) a lower plate forming a top surface and an opposite sternum-facing surface, and having a bone fixation region with at least one countersunk aperture for receiving a fastening means for affixing said sternum-facing surface of said upper plate to one side of the sternum, and a locking region with at least one aligning member protruding approximately perpendicular to the top surface of said plate;
    b) an upper plate forming a top surface and an opposite sternum-facing surface, and having a bone fixation region with at least one countersunk aperture for receiving a fastening means for affixing said sternum-facing surface of said second said plate to an opposite side of the sternum, and an attached aperture dimensioned to overlap with at least a portion of said locking region of said lower plate; and
    c) a rotating member having at least one aperture dimensioned to engage with said at least one protruding aligning member, wherein said rotating member holds said lower and upper plates together to secure opposite sides of the sternum when rotated in a first direction, further wherein said rotating member can be removed and said lower and upper plates separated by reversely rotating said rotating member to disengage said rotating member from at least one aligning member.

12. A method of treating a sternal fracture comprising affixing to a patient the sternal closure device of claim 11.

13. A method of treating a sternal fracture using the sternal closure device of claim 11, the method comprising:
    a) affixing said lower plate to one side of the sternum using said fastening means through said at least one countersunk aperture;

b) affixing said upper plate to opposite side of the sternum using said fastening means through said at least one countersunk aperture; and
c) holding said first and second plates together by engaging said rotating member with said at least one aligning member on said first plate.

14. The device of claim 1, wherein said first plate further comprises at least one depressible pin and said rotating member further comprises at least one aperture that engages with said pin.

15. The device of claim 14, wherein engagement of said rotating member with said pin(s) prevents said rotating member from rotating, and further wherein depression of said pins disengages said rotating member from said pins to allow rotation and disengagement of said rotating member from said aligning members.

16. The device of claim 11, wherein said first plate further comprises at least one depressible pin and said rotating member further comprises at least one aperture that engages with said pin.

17. The device of claim 16, wherein engagement of said rotating member with said pin(s) prevents said rotating member from rotating, and further wherein depression of said pins disengages said rotating member from said pins to allow rotation and disengagement of said rotating member from said aligning members.

18. The device of claim 14, wherein said at least one aperture on said rotating member that engages with said pin is formed through said rotating member to allow selectively depressing said pin.

19. The device of claim 1, wherein said at least one aperture on said rotating member that engages with said at least one aligning member comprises a countersunk portion to receive said at least one aligning member.

20. The device of claim 16, wherein said at least one aperture on said rotating member that engages with said pin is formed through said rotating member to allow selectively depressing said pin.

21. The device of claim 11, wherein said at least one aperture on said rotating member that engages with said at least one aligning member comprises a countersunk portion to receive said at least one aligning member.

22. The device of claim 1, wherein said rotating member is removable from at least one of said first plate or said second plate.

23. The device of claim 1, wherein said at least one aligning member comprises at least two aligning members, and wherein said at least one aperture on said rotating member that engages with said at least one aligning member comprises at least two apertures.

24. The device of claim 11, wherein said at least one aligning member comprises at least two aligning members, and wherein said at least one aperture on said rotating member that engages with said at least one aligning member comprises at least two apertures.

* * * * *